US007141382B1

(12) United States Patent
Parikh et al.

(10) Patent No.: US 7,141,382 B1
(45) Date of Patent: Nov. 28, 2006

(54) METHODS FOR DETECTION OF IL-18 AS AN EARLY MARKER FOR DIAGNOSIS OF ACUTE RENAL FAILURE AND PREDICTOR OF MORTALITY

(76) Inventors: Chirag R. Parikh, 8300 Fairmount Dr., PP-102, Denver, CO (US) 80247; Charles L. Edelstein, 1011 S. Valentia St., #78, Denver, CO (US) 80247

( * ) Notice: Subject to any disclaimer, the term of this patent is extended or adjusted under 35 U.S.C. 154(b) by 0 days.

(21) Appl. No.: 10/964,201

(22) Filed: Oct. 12, 2004

(51) Int. Cl.
*G01N 33/53* (2006.01)

(52) U.S. Cl. ...................... 435/7.1; 435/7.92; 436/518

(58) Field of Classification Search ................ 435/7.1, 435/7.92; 436/524, 536, 518
See application file for complete search history.

(56) References Cited

U.S. PATENT DOCUMENTS

| | | | | |
|---|---|---|---|---|
| 4,959,302 | A * | 9/1990 | Cornaby et al. | 435/5 |
| 5,912,324 | A | 6/1999 | Okamura et al. | |
| 5,914,253 | A | 6/1999 | Okamura et al. | |
| 6,197,297 | B1 | 3/2001 | Kunikata et al. | |
| 6,214,584 | B1 | 4/2001 | Ushio et al. | |
| 6,274,709 | B1 | 8/2001 | Okamura et al. | |
| 6,277,598 | B1 | 8/2001 | Okamura et al. | |
| 6,509,449 | B1 | 1/2003 | Kunikata et al. | |
| 6,589,764 | B1 | 7/2003 | Sims et al. | |
| 6,600,022 | B1 | 7/2003 | Torigoe et al. | |
| 6,706,487 | B1 | 3/2004 | Abdel-Meguid et al. | |
| 2003/0099607 | A1 | 5/2003 | Okimura et al. | |
| 2004/0023336 | A1 | 2/2004 | Heavner et al. | |

FOREIGN PATENT DOCUMENTS

| | | | |
|---|---|---|---|
| EP | 0 974 600 | A2 | 1/2000 |
| EP | 0 861 683 | A3 | 3/2000 |
| EP | 1 101 772 | A1 | 5/2001 |
| EP | 1 110 969 | A1 | 6/2001 |
| WO | WO 01/58956 | A2 | 8/2001 |

OTHER PUBLICATIONS

Melnikov et al."Impaired IL-18 processing protects caspase-1-deficient mice from ischemic acute renal failure" (2001) J. Clin, Invest. 107:1145-1152.*

Chiang et al. "Interleukin-18 is a strong predictor of hospitalization inhaemodialysis patients" (2004) Nephrology Dialysis Transplantation 19:2810-2815.*

Melnikov et al. Journal of the American Society of Nephrology, (Sep. 2002) vol. 13, Program and Abstracts Issue pp. 143A. Meeting Info: Meeting of the American Society of Nephrology, Philadelphia, PA, USA, Oct. 30-Nov. 4, 2002.*

Simon et al. "Serial peripheral blood interleukin-18 and perforin gene expression measurements for prediction of acute kidnet graft rejection" (May 27, 2004) Transplantation 77:1589-1595.*

Parikh et al. "Urinary Interleukin-18 Is a Marker of Human Acute Tubular Necrosis" (Mar. 2004) American Journal of Kidney Diseases 43:405-414.*

Parikh et al., Journal of the American Society of Nephrology, (Nov. 2003) vol. 14, Abstracts Issue, p. 278A-279A. Meeting of the American Society of Nephrology Renal Week, San Diego, CA, USA, Nov. 12-17, 2003.*

Hu et al. "Serum Profiles of IL-12, -15, and -18 in Renal Allograft Dysfunction in Man" (2003) Transplantation Proceedings 35:246-248.*

Nakae et al. "Involvement of IL-18 and soluble fas in patients with postoperative hepatic failure" (2003), Eur Surg Res 35:61-66.*

Affleck et al., "Interleukin-18 Production Following Murine Cardiac Transplantation: Correlation with Histological Rejection and the Induction of IFN-g" (2001) Journal of Interferon and Cytokine Research 21:1-9.*

Peeters et al., "Delayed graft function in renal transplantation" (2004) Current Opinion in Critical Care 10:489-498.*

Nakamura et al. "Serum Interleukin-18 Levels Are Associated With Nephropathy and Atherosclerosis in Japanese Patients With Type 2 Diabetes" (2005) Diabetes Care 28:2890-2895.*

Daemen et al. "Ischemia/Reperfusion-Induced IFN-gamma Up-Regulation: Involvement of IL-12 and IL-18" (1999) The Journal of Immunology 162:5506-5510.*

Parikh et al. "Urine IL-18 is an early diagnostic marker for acute kidney injury and predicts mortality in the intensive care unit" J. Am. Soc. Nephrol. (2005) 16(10): 3046-52.*

Abreo K et al., Changing patterns and outcome of acute renal failure requiring hemodialysis. Arch Itern Med 1986;146(7):1338-41.

Åhlström A et al., Predictive value of interleukins 6, 8 and 10, and low HLA-DR expression in acute renal failure. Clin Nephrol 2004;61(2):103-10.

Allgren RL et al., Anaritide in acute tubular necrosis. Auriculin Anaritide Acute Renal Failure Study Group. N Engl J Med 1997;336(12):828-34.

Ketoconazole for early treatment of acute lung injury and acute respiratory distress syndrome: a randomized controlled trial. The ARDS Network Authors, The ARDS Network. JAMA 2000;283(15):1995-2002.

Biesenbach G et al., Improvement in prognosis of patients with acute renal failure over a period of 15 years: an analysis of 710 cases in a dialysis center. Am J Nephrol 1992;12(5):319-25.

Casey LC et al., Plasma cytokine and endotoxin levels correlate with survival in patients with the sepsis syndrome. Ann Intern Med 1993;119(8):771-8.

(Continued)

*Primary Examiner*—Long V. Le
*Assistant Examiner*—Christine E. Foster
(74) *Attorney, Agent, or Firm*—Faegre & Benson LLP

(57) ABSTRACT

The present disclosure concerns methods of detecting a molecule, interleukin 18, in a sample, and using the detection of IL-18 to predict a condition. In a particular embodiment, the present invention concerns methods of detecting interleukin 18, in a sample, preferably prior to the increase in serum creatinine in a subject predisposed to a condition. In certain embodiments, the methods may comprise obtaining a sample from a subject such as a urine or blood sample and analyzing the sample for the presence or absence of IL-18 to predict a condition for example acute renal failure or organ transplant failure. In another embodiment, the methods may comprise analyzing a sample from a subject for the presence of IL-18 and applying information obtained from analyzing the presence of IL-18 to determine a treatment for a medical condition of the subject.

11 Claims, 2 Drawing Sheets

OTHER PUBLICATIONS

Chertow GM, et al., Independent association between acute renal failure and mortality following cardiac surgery. Am J Med 1998;104(4):343-8.
de Mendonça A et al., Acute renal failure in the ICU: risk factors and outcome evaluated by the SOFA score, Intensive Care Med 2000;26(7):915-21.
Dinarello CA. Biologic basis for interleukin-1 in disease. Blood 1996;87(6):2095-147.
du Cheyron D et al., Urinary measurement of Na+/H+ exchanger isoform 3 (NHE3) protein as new marker of tubule injury in critically ill patients with ARF. Am J Kidney Dis 2003;42(3):497-506.
Emmanuilidis K et al., Differential regulation of systemic IL-18 and IL-12 release during postoperative sepsis: high serum IL-18 as an early predictive indicator of lethal outcome, Shock 2002;18(4):301-5.
Fantuzzi G et al., Interleukin-18 regulation of interferon gamma production and cell proliferation as shown in interleukin-1beta-converting enzyme (caspase-1)-deficient mice. Blood 1998;91(6):2118-25.
Gogos CA, et al., Pro-versus anti-inflammatory cytokine profile in patients with severe sepsis: a marker for prognosis and future therapeutic options. J Infect Dis 2000;181(1):176-80.
Groeneveld AB et al., Acute renal failure in the medical intensive care unit: predisposing, complicating factors and outcome. Nephron 1991;59(4):602-10.
Han WK, et al., Kidney Injury Molecule-1 (KIM-1): a novel biomarker for human renal proximal tubule injury. Kidney Int 2002;62(1):237-44.
Hirschberg R et al., Multicenter clinical trial of recombinant human insulin-like growth factor I in patients with acute renal failure. Kidney Int 1999;55(6):2423-32.
Hoste EA et al., Acute renal failure in patients with sepsis in a surgical ICU: predictive factors, incidence, comorbidity, and outcome. J Am Soc Nephrol 2003;14(4):1022-30.
Kwon O et al., Urinary actin, interleukin-6, and interleukin-8 may predict sustained ARF after ischemia injury in renal allografts. Am J Kidney Dis 2003;41(5):1074-87.
Levy Em et al., The effect of acute renal failure on mortality. A cohort analysis. Jama 1996;275(19):1489-94.
Lien J et al., Risk factors influencing survival in acute renal failure treated by hemodialysis. Arch Intern Med 1985;145(11):2067-9.
Melnikov VY et al., Neutrophil-independent mechanisms of caspase-1- and IL-18-mediated ischemia acute tubular necrosis in mice. J Clin Invest 2002;110(8):1083-91.
Metnitz PG et al., Effect of acute renal failure requiring renal replacement therapy on outcome in critically ill patients. Crit Care Med 2002;30(9):2051-8.
Miller TR et al., Urinary diagnostics indices in acute renal failure: a prospective study. Ann Intern Med 1978;89(1):47-50.
Mishra J et al., Identification of neutrophil gelatinase-associated lipocalin as a novel early urinary biomarker for ischemia renal injury. J Am Soc Nephrol 2003;14(10):2534-43.
Muramatsu Y et al., Early detection of cysteine rich protein 61 (CYR61, CCN1) in urine following renal ischemic reperfusion injury. Kidney Int 2002;62(5):1601-10.
Ventilation with lower tidal volumes as compared with traditional tidal volumes for acute lung injury and the acute respiratory distress syndrome. The Acute Respiratory Distress Syndrome Network. N Engl J Med 2000;342(18):1301-8.
Parikh CR et al., Renal dysfunction in allogeneic hematopoietic cell transplantation. Kidney Int 2002;62(2):566-73.
Pinsky MR et al., Serum cytokine levels in human septic shock. Relation to multiple-system organ failure and mortality. Chest 1993;103(2):565-75.
Rabb H, Novel urinary markers for early diagnosis of ARF. Am J Kidney Dis 2003;42(3):599-600.
Ranieri VM et al., Mechanical vetilation as a mediator of multisystem organ failure in acute respiratory distress syndrome. JAMA 2000;284(1):43-4.
Shibata M et al., Increased concentrations of plasma IL-18 in patients with hepatic dysfunction after hepatectomy. Cytokine 2000;12(10):1526-30.
Shusterman N et al., Risk factors and outcome of hospital-acquired acute renal failure. Clinical epidemiologic study. Am J Med 1987;83(1):65-71.
Simmons EM et al., Plasma cytokine levels predict mortality in patients with acute renal failure. Kidney Int 2004;65(4):1357-65.
Star R, Design issues for clinical trials in acute renal failure. Blood Purif 2001; 19(2):233-7.
Star RA., Treatment of acute renal failure. Kidney Int 1998;54(6):1817-31.
Stone GW et al., Fenoldopam mesylate for the prevention of contrast-induced nephropathy: a randomized controlled trial. Jama 2003;290(17):2284-91.
Westhuyzen J et al., Measurement of tubular enzymuria facilitates early detection of acute renal impairment in the intensive care unit. Nephrol Dial Transplant 2003;18(3):543-51.
Zarich S et al., Fractional excretion of sodium; exceptions to its diagnostics value. Arch Intern Med 1985;145(1):108-12.

* cited by examiner

| IL-18 cut-off (pg/ml) | Sensitivity | Specificity | PPV | NPV |
|---|---|---|---|---|
| 10 | 0.75 | 0.62 | 0.49 | 0.84 |
| 25 | 0.74 | 0.66 | 0.5 | 0.82 |
| 50 | 0.59 | 0.71 | 0.5 | 0.78 |
| 100 | 0.5 | 0.85 | 0.62 | 0.78 |
| 200 | 0.41 | 0.91 | 0.68 | 0.76 |
| 500 | 0.19 | 0.98 | 0.86 | 0.71 |

METHODS FOR DETECTION OF IL-18 AS AN EARLY MARKER FOR DIAGNOSIS OF ACUTE RENAL FAILURE AND PREDICTOR OF MORTALITY

This invention was made with government support under grants K23-DK064689 and RO1-grant number DK56851 from the National Institutes of Health. The government has certain rights in this invention

FIELD

The present invention relates to methods for detection of interleukin (IL-18) in a sample for use in diagnosis of a condition. In certain embodiments, the disclosed methods may be used to identify IL-18 in a sample of a patient predisposed to renal failure. In other embodiments, the disclosed methods may be used to identify IL-18 in urine of a patient predisposed to acute renal failure (ARF). In another embodiment, a method for detection of IL-18 in a sample may include detecting IL-18 shortly after organ injury by detecting the presence of the protein in a sample using a specific IL-18 antibody assay. In a particular embodiment, IL-18 may be detected in a sample after organ injury and before elevation in serum creatinine. The disclosed methods are of use to assess an individual's health, particularly renal health and if needed to intervene with an appropriate treatment.

BACKGROUND

Acute renal failure (ARF) occurs in approximately 1% to 25% of critically ill patients depending upon the population being studied and the criteria used to define its presence. For example, ARF complicating a nonrenal organ failure in the intensive care unit (ICU) is associated with a mortality of around 50% to 70%. This statistic has not improved significantly over the last five decades (1–7). In addition, it is well established that the development of ARF is independently associated with an increase in mortality (2, 8–11).

In the past, several agents have been used as potential treatments of ARF to impact the high mortality associated with ARF; however, none of them have been successful. One principle reason for the failure of these therapeutic interventions in clinical trials of ARF is the dependency of serum creatinine as a screening process for initial enrollment of patients, for the diagnosis of ARF and for initiating the intervention. ARF has been typically diagnosed by a progressive rise in serum creatinine over several days, which may or may not be associated with oliguria, (decreased urine output for example producing less than 500 ml of urine in 24 hours).

Because of the vital importance of earlier administration on the success rate of therapies, many markers have been explored for early diagnosis of ARF. Several cytokines and molecules have been analyzed as potential early markers of ARF. Although the initial studies on some molecules like tubular enzymes, growth factors, adhesion molecules and some cytokines (14–16, 29–31) were promising, subsequent studies have shown inadequate sensitivity or specificity to advocate clinical use for diagnosis. Recently described molecules such as kidney injury molecule-1 (KIM-1), cysteinrich protein 61 (Cry61), neutrophil gelatinase-associated lipocalin (NGAL) and sodium/hydrogen exchanger isoform 3 (NHE3) have demonstrated results as markers of ARF at the pre-clinical level (14–16, 29–31). However, to date, none of these molecules have been systematically explored in human ARF diagnosis.

Renal hypoperfusion or ischemia account for about 50% of the cases of ARF (1, 2). The main functional problem in these patients is a decrease in GFR (glomerular filtration rate) and its consequent effects on uremic toxin accumulation, fluid, electrolyte and acid-base balance. The course of the illness is highly variable ranging from a transient disease lasting less than one week and associated with full recovery of renal function, to a disease persisting for longer than one month and requiring dialysis and intensive care management. There is no clear relationship between the severity of the initial ischemic insult and the course of the illness. However, there is a correlation between the duration of the kidney dysfunction and mortality from ARF. Fresh renal ischemic lesions have been found in biopsy or autopsy specimens of patients with ARF as late as 3 weeks after the initial ischemic event (4). Thus, a better understanding of the pathogenesis of ARF is needed to allow interventions which would prevent the need for hemodialysis, shorten the course of ARF and improve survival. The virtual complete recovery of renal function in those patients who survive ARF, as well as the minimal renal histological abnormalities during ARF when the GFR is less than 10 ml/min, suggest that there are reversible components in the pathophysiology of ARF. In addition, ARF is a common life threatening complication following allogeneic hematopoietic stem cell transplant (HSCT), previously termed a bone marrow transplant, Thus, early detection of ARF is imperitive for early intervention and treatment.

Because early intervention of renal disfunction is critical, a need exists for the detection of early signs that predict the onset of the condition. The present invention, concerns the detection of an indicator molecule to predict the onset of organ failure. The detection of this indicator can alert a medical practitioner that treatment may be required immediately to attenuate the condition and possibly prevent full onset of organ shutdown and death.

SUMMARY

The present invention relates to methods for evaluating the presence of IL-18 in a sample to assess a condition. In an exemplary IL-18 assay, a sample from a subject is obtained, IL-18 is detected and based on this information the condition of a subject is evaluated. IL-18 presence is assessed in the sample, preferably using an antibody assay, to evaluate the presence or absence of IL-18 or an individual's concentration of IL-18 at a given time. This information may then be used to analyze the condition of a subject, for example the status of an organ such as the kidneys or lungs. In particular embodiments, the form of IL-18 detected can be the pro form or the mature form detected in a sample using an enzyme-linked assay (ELISA) directed to a form of IL-18. From such analysis, the propensity for organ failure such as renal failure may be determined using the information obtained on the presence or concentration of IL-18 in a sample.

In certain embodiments, a sample from a subject with acute respiratory distress syndrome (ARDS) is obtained and IL-18 is analyzed. In certain embodiments, urine or blood samples at different times from a subject with ARDS may be obtained and analyzed for IL-18 presence or concentration and this information may be used to assess the condition of the subject. In one example, these samples may be samples that do not have an increase of serum creatinine detected in the subject's blood. The disclosed methods allow the rapid assessment of organ health of a patient such as the renal health of a patient predisposed to ARF.

In another embodiment, at least one sample from a subject admitted to the intensive care unit may be obtained and analyzed for IL-18 and the subject evaluated based on the information obtained on IL-18. In certain embodiments, urine or blood samples at different times from a subject admitted to the intensive care unit may be obtained and analyzed for the presence or absence of IL-18. In one example, multiple parameters of an admitted subject, such as age and gender, may be examined in combination with the IL-18 factor to assess the survivability of a subject. In addition, the criteria may be used to assess the efficacy of treatment of the subject with at least one therapeutic agent.

In particular embodiments, IL-18 assessment may be performed in a container or test cell, including but not limited to 96-well microtiter plates, into which the sample (such as fresh centrifuged or freeze-thawed, urine sample) and appropriate reagents have been added. In another embodiment, IL-18 assessment may be performed using a detection system where the sample is directly assayed using an antibody-coated unit such as an indicator stick method that readily identifies the presence or absence or concentration of IL-18 within the sample. An exemplary apparatus of use in the disclosed methods may include a sample, one or more reagents, buffer, a reagent chamber, and a detection instrument, such as an ELISA reader. In more particular embodiments, the reagents added to the reagent chamber may include the sample, IL-18 antibody and a buffer. Where exemplary containers exhibit multiple sample compartments, such as a 96-well plate, the sample may preferably be analyzed in replicates, such as triplicate wells of a 96-well plate. An advantage of the disclosed methods is that the amount of sample required to assay may be relatively small.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

Figure 1:
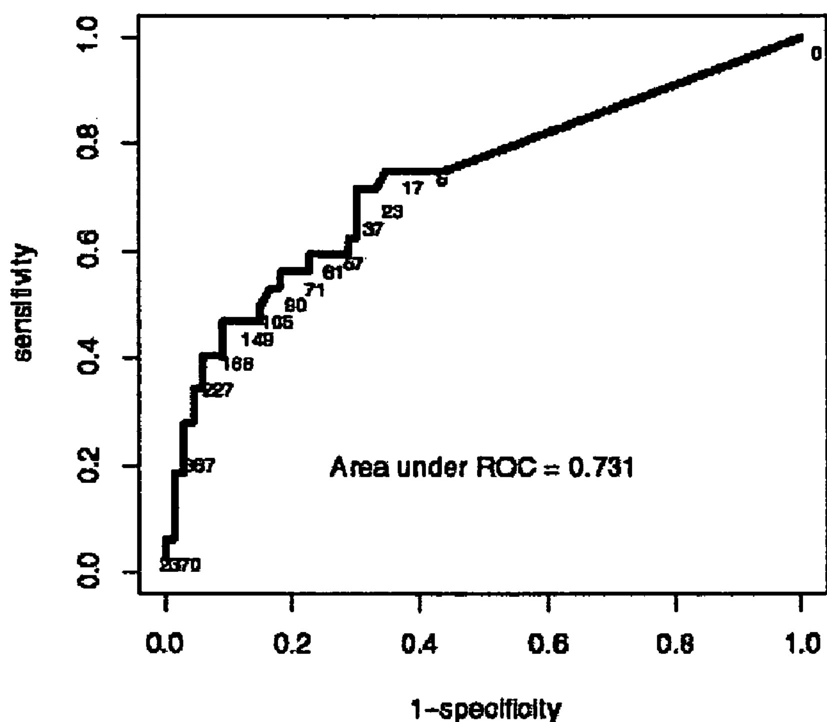
FIG. 1. represents an exemplary plot of IL-18 measured one day before ARF.

Table 1 represents an exemplary compilation of baseline characteristics of patients in a study used for analysis.

Table 2 represents an example of biochemical parameters of patients and survival of these individuals.

Table 3A and 3B represent examples of multvariable tables compiled for prediction of ARF 24 (3A) and 48 (3B) hours prior to clinical diagnosis of ARF.

Table 4 represents a proportional hazards model for time to death based on baseline covariates.

DESCRIPTION OF ILLUSTRATIVE EMBODIMENTS

Definitions

Terms that are not otherwise defined herein are used in accordance with their plain and ordinary meaning.

As used herein, "a" or "an" may mean one or more than one of an item.

DETAILED DESCRIPTION

In the following section, several embodiments of, for example, methods are described in order to thoroughly detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description in order to prevent unnecessary masking various embodiments.

Pathophysiology of Acute Renal Failure

In spite of advances in the management of critically ill patients and technological advances in renal replacement therapy, the mortality rate of patients with ARF remains high. Since therapies have advanced and more complicated surgical interventions in older and multimorbid patients are applied, the number of patients with ARF is increasing. In addition, ARF itself increases predisposition to other complications that can be deleterious. In one study, it was demonstrated that ARF was associated with mortality in patients following administration of radiocontrast media in an intensive care unit and in patients following cardiac surgery. Thus, early prediction and/or intervention of ARF is required in order to decrease the mortality rate of patients undergoing these treatments as well as others.

The Nature of Renal Cell Injury

A decrease in glomerular filtration rate (GFR) is the principle functional change in patients with acute renal failure (ARF). In one study, patients with a near complete recovery of renal function, as well as the minimal renal histological abnormalities during ARF when the GFR is less than 10 ml/min, suggested that a major component of the renal tubular cell injury may be sublethal and as noted here, reversible. Experimental models of acute tubular necrosis frequently have placed the emphasis on irreversible proximal tubular cell death. The nature of the renal tubular cell injury in ischemic acute renal failure, however, includes not only cell death (necrosis or apoptosis) but also sublethal injury causing cell dysfunction. Thus, in order to prevent ARF progression by intervention, early detection of the onset of the condition is required

General Considerations for Early IL-18 Detection

In one embodiment, the present invention concerns the role of detecting IL-18 in a sample of a subject for prediction of the onset of ARF and intervention of its progression. Recently, it was demonstrated that IL-18 mediates ischemic ARF in mice. The pro-inflammatory cysteine protease caspase-1 converts the pro form to the mature (active) form of IL-18 in ischemic ARF in mice. Caspase inhibition in knock out animals and IL-18 blockage by neutralizing antibodies not only provide functional protection, but also prevent histological changes of ARF. It is suggested that the active form of IL-18 exits the cell and may enter the urine after being activated in the proximal tubules. The presence of IL-18 in the tubular lumen was confirmed by immunohistochemistry and by its detection in the mouse urine. Experiments have shown that urinary IL-18 concentrations were increased in mice with ischemic ARF, also known as acute tubular necrosis (ATN), compared with the sham-operated mice (control group: surgical procedure only). These early observations led to the hypothesis that IL-18 in urine had the potential to serve as a biomarker for ARF onset in humans. Thus, IL-18 studies of patients with different forms of ARF were performed.

Ultimately, it was observed that the urine IL-18 levels were significantly increased in patients with clinical ATN as compared to prerenal ARF, urinary tract infection, chronic renal insufficiency and nephritic syndrome. The correlation revealed that urinary IL-18 levels had sensitivity and specificity of >90% for diagnosis of established ATN in humans.

Acute Respiratory Distress Syndrome and ARF

Acute Respiratory Distress Syndrome (ARDS) is a common diagnosis in the ICU and is commonly associated with ARF. Urine samples of ICU patients revealed that IL-18 is an early marker of ARF in the patients diagnosed with ARDS. The studies utilized the tissue samples collected during the ARDS patient interventional trials. The observation of IL-18 in these patients precedes the clinical diagnosis of ARF. A urine IL-18 test is quick, easy, reliable and fairly inexpensive. Because ARDS is a common diagnosis in the ICU and is commonly associated with ARF, detection of IL-18 as an early marker of ARF in the ICU patients with ARDS may ultimately decrease the mortality rate. The urine IL-18 levels precede the clinical diagnosis of ARF in ARDS patients and thus provide early intervention to augment or possibly prevent ARF. In one embodiment, a sample may be tested for the presence of IL-18 to assess the condition of a subject. In another embodiment, the sample may be a urine sample from a subject at risk for renal disease. In another embodiment, a sample from a subject may be tested for the presence of IL-18 shortly after renal injury to the subject. In another embodiment, a urine sample may be tested for the presence of IL-18 prior to the appearance of serum creatinine in the sample. In another embodiment, a urine sample from an intensive care patient may be tested for the presence of IL-18 after renal injury and prior to the appearance of increased serum creatinine. These assays can be used on a large scale to clinically establish early diagnosis or screening for ARF.

Healthcare providers are in need of an inexpensive and easily administered test for early predictors of organ failure. In one example, a quick and inexpensive test for the prediction of ARF is needed. In other examples, a quick and inexpensive test for the prediction of lung or liver failure is needed. Because of the nature of ARF as a predictor of mortality of a patient such as an ICU patient, a method that can warn a healthcare provider that ARF is most probable would be extremely beneficial from a clinical perspective. This information can alert the health care provider that intervention by a therapeutic treatment may be required immediately. The application of such methods is important for patients with the potential for organ failure such as renal failure for example in ARDS patients. In addition, the application of such methods is important for patients undergoing a transplantation such as renal transplantation. Other situations where these techniques may be extremely useful include liver, lung, heart and bonemarrow transplants.

Methods for detection of IL-18 in a sample are disclosed herein. A relatively cheap, quick and reliable assay will promote optimal application of a health provider's resources to diagnose organ insufficiencies such as renal insufficiencies and other conditions of altered renal function, to monitor response to drug regimen and enhance treatment efficiency, leading to a decreased loss of life and decreased cost.

Advantages of the IL-18 Assay

Advantages of the IL-18 assay include reliable results that correlate with organ health. Because the assay utilizes a simple detection method, the reproducibility and reliability of the test will provide accurate sample analysis. The equipment and methodologies used to analyze the presence of IL-18 does not require any extensive training of the operator. The assay is straightforward since antibody kits are available The assay is very sensitive and requires a short time period, typically in the time range of three hours or less. Since the IL-18 assay measures IL-18 early in disease progression, it provides more complete data than presently used methods for early intervention and treatment.

The IL-18 assay typically discloses the presence of IL-18 sometime after organ insult such as renal injury. The evaluation of the presence of IL-18 in the context of other parameters has suggested that the IL-18 assay is sensitive to altered states of organ health, including renal, and lung in critically ill patients.

Disadvantages of Present Assay Systems

Because of the vital importance of earlier targeting of therapies, many markers have been explored for early diagnosis of ARF. Several cytokines and molecules have been suggested to have a potential role as early markers of ARF. Although the initial studies on some molecules like tubular enzymes, growth factors, adhesion molecules and some cytokines (14–16, 29–31) were promising, the larger and more detailed studies have shown inadequate sensitivity or specificity to advocate clinical use. Recently described molecules such as kidney injury molecule-1 (KIM-1), cysteinrich protein 61 (Cry61), neutrophil gelatinase-associated lipocalin (NGAL) and sodium/hydrogen exchanger isoform 3 (NHE3) have demonstrated compelling results as markers of ARF at the pre-clinical level (14–16, 29–31). However, none of these molecules have been systematically explored in human ARF. These molecules differ in their ease of measurement, reproducibility and specificity in distinguishing between various forms of ARF. KIM-1 can be measured easily with ELISA. KIM-1 was documented in patients with established ischemic renal damage; however, its detection as an early diagnostic marker of ARF has not been validated (15). Urine NHE3 protein appears to have excellent correlation with the clinical diagnosis of ARF, but the performance of this test as an early marker also needs to be determined (30). The NHE3 protein is measured by immunobloting, therefore the rigorous and long turn-around time of the assay compromises the potential clinical utility of this measure. Cry61 is secreted early in ARF in the urine in rats, but the detection requires a bioaffinity purification step with heparin-sepharose beads (14). NGAL also appears in the urine very early in ARF in rats and is detected by Western blotting (16). The performance of CRY61 and NGAL as a biomarker of ARF has not been reported in humans. In one embodiment, the detection of IL-18 in a sample may be combined with detection of any of the aformentioned early markers of organ failure or transplant rejection. For example IL-18 may be detected in conjunction with any combination of KIM-1, NHE3, Cry61 or NGAL.

FeNa has been suggested to be a marker of renal dysfunction (32). It was originally described as <1% in prerenal azotemia and >1% in ARF due to intrarenal causes (32). However, FeNa can be low in nonoliguric ARF, sepsis, urinary tract obstruction, hepatorenal syndrome and acute glomerulonephritis (33). Thus, the specificity of FeNa and its clinical utility in ARF are diminished due to these false negatives. Therefore the results of FeNa must be interpreted in the context of rising creatinine or falling urine output. Accordingly, the applicability of FeNa as an early marker of ARF is limited due to false positive results in healthy patients. In one example of the present study, FeNa was not different in ARF and controls. A recent prospective study also demonstrated that FeNa is not a reliable marker of tubular injury in critically ill patients (31).

Serum Creatinine

Currently used in clinical practice and in clinical trials, the serum creatinine analysis has been found to be a poor marker of renal dysfunction. Unlike serum troponin in myocardial infarction, an increase in serum creatinine is not directly related to tubular injury in ARF, but is the effect of loss of filtration function that occurs with ARF. There is also a delay in the detectable increase in serum creatinine due to the time required for its accumulation and equilibration. The increase in creatinine may also be masked by intravenous volume administration. Changes in creatinine can be non-specific as they may occur due to several non-renal factors (12). This lack of sensitivity and specificity of serum creatinine in the diagnosis of ARF has been the main hurdle in the development of therapeutic interventions in the setting of ARF. In contrast to creatinine, IL-18 is a proinflammatory cytokine that is released in response to tissue injury. Studies in mice have demonstrated the role of IL-18 as a mediator of ischemic ARF (21, 22). Subsequently, urine IL-18 was shown to be present with >90% sensitivity and specificity in the urine of patients with established ARF (25). Like the decades old serum creatinine assay, the detection of IL-18 is also a simple, rapid and inexpensive test. In one example, the test utilizes the common ELISA methodology with the capability to assay up to 96 samples at a time and has a turn-around time of 3 hours.

The disadvantages that each of these assays compared to assessing the presence of IL-18 as presented herein are the lack of total assessment of a sample over a given time, the rapid turnaround of results and the ease of use of the assay kit. The detection of IL-18 is important in understanding the physiological process of organ failure particularly in order to accurately diagnose and treat conditions associated with these systems at an early stage in disease or condition progression.

Uses of IL-18 Assay

Evaluating and Monitoring the Appearance of IL-18

Whether or not organ (or cellular) destruction can be minimized after events such as organ injury or insult may depend, in part, upon the early introduction of therapeutically relevant treatments. In order to eliminate, minimize or attenuate such destruction in an individual who has undergone or is undergoing organ failure or similar event, it would be helpful to predict these events earlier in progression rather than later. By comparing the individual's specific level of IL-18 to a normal healthy control, or within a given individual over time, a treating physician could determine whether the patient needs to be treated immediately or otherwise observed for a period of time.

Under conditions when IL-18 is detected in a sample of a subject, such as after organ injury or organ transplant, it becomes critical that the treating healthcare provider have reliable information available about an individual's concentration of IL-18 in the sample. For example, a high concentration of IL-18 (for example >1000 pg/ml) is especially likely to occur when the subject is undergoing a delayed kidney transplant graft function. In addition, a high concentration of IL-18 (for example >100 pg/ml) is especially likely to occur when an ARDS subject has experienced renal insult. Thus, when a patient's organ activity such as renal activity is impaired, a healthcare professional may intervene and administer a therapeutic treatment to attenuate the failure of the organ to avoid the possibility of permanent damage or death of the patient. In addition, a healthcare professional may monitor the therapeutic treatment of the subject by obtaining samples from the patient after treatment and analyzing the presence of IL-18 in the sample and assessing the condition of the patient based on these findings. Therapeutic treatments may be altered depending on the continued presence of IL-18 or the concentration of IL-18 present in the sample.

IL-18 and Transplantation

Acute renal failure (ARF) is a common life-threatening complication after myeloablative allogeneic hematopoietic cell transplantation (HCT). One current technique to eradicate the malignancy with graft-versus-tumor effect is non-myeloablative HCT, rather than with high doses of chemo-radiotherapy. In one study (incorporated by reference, Parikh et al J. Am Soc. Nephrol. 2003 July; 15(7): 1868–76), a large group of patients received nonmyeloablative HCT. This cohort study enrolled patients who were undergoing nonmyeloablative HCT at four major centers from 1998 to 2001. The data in this study suggested that ARF may contribute to mortality after nonmyeloablative HCT. (Parikh et al J. Am Soc. Nephrol. 2003 July; 15(7): 1868–76). IL-18 is indicator of early ARF onset. Thus, an early indication of ARF by IL-18 detection may be important in intervention of progression of the condition.

Activation of IL-18 and Caspases

The caspases are a family of intracellular cysteine proteases. Caspases participate in two distinct signaling pathways: (a) activation of proinflammatory cytokines by caspase-1 (previously known as IL-1β-converting enzyme, or ICE), and (b) promotion of apoptotic cell death via caspase-3. In culture, the inhibition of caspases protects against necrotic cell death induced by hypoxia in renal tubules and freshly isolated rat proximal tubules. In rat kidneys with acute tubular necrosis (ATN), both caspase-1 and capase-3 mRNA and protein expression as well as caspase-3 activity are increased. Caspase inhibition attenuates distal tubule apoptosis and inflammation in ischemic acute renal failure (ARF) in mice. However, the effect of caspase inhibitors on ATN, the predeominant pathological process in animal models of ischemic ARF and in posttransplant ARF in humans, is not known. (Melnikov et al., Journal of Clinical Investigation, October 2002 vol. 110 No.8.p. 1083–91)

The proinflammatory caspase-1 plays a major role in the cleavage of the IL-18 precursor. Caspase-1 is remarkably specific for the precursors IL-18 (IFN-γ-inducing factor) by making a single initial cut in each procytokine, which results in an active mature cytokine secreted into the extracellular space. It was demonstrated that caspase-1-deficient mice are functionally and histologically protected against ischemic ARF and that this protection is associated with decreased conversion of IL-18 precursor to the mature form in the kidney (Melnikov et al., Journal of Clinical Investigation, October 2002 vol. 110 No.8.p. 1083–91)

IL-18 and Proximal Tubules.

One study demonstrated an increase in IL-18 in the urine of mice with ischemic ARF incorporated herein by reference (Melnikov et al., Journal of Clinical Investigation, October 2002 vol. 110 No.8.p. 1083–91). Here, proximal tubules were analyzed as the possible source and target of IL-18. Studies were performed on freshly isolated proximal tubules from C57BL/6 mice. OPH-001, a pancaspase inhibitor, protected against 25 minutes of hypoxic injury in these tubules. LDH release was 11%±1% in normoxic tubules, 38%±6% in hypoxic tubules preincubated with vehicle (DMSO) (P<0.001 vs. normoxia, n=6), and 22%±1% in hypoxic tubules preincubated with OPH-001 (100 μM) (P<0.01 vs. hypoxia, n=6). Immunoblotting (n=6) of normoxic proximal tubules demonstrated the presence of pro-IL-18 (24 kDa). Exogenous recombinant IL-18 (1 μg per 6 ml of tubule suspension) exacerbated sublethal (12 minutes) hypoxic proximal tubular injury. LDH release was 10%±1% in normoxic tubules, 13%±1% in hypoxic tubules preincubated with vehicle (saline) (NS vs. normoxia, n=6), and 18%±1% in hypoxic tubules preincubated with recombinant IL-18 before induction of hypoxia (P<0.01 vs. hypoxia, n=6). Thus, it appears that IL-18 plays a role in hypoxic injury of proximal tubules. (Melnikov et al., Journal of Clinical Investigation, October 2002 vol. 110 No.8.p. 1083–91). Another source of IL-18 are T lymphocytes and monocytes. It is possible that these cells are a source of IL-18 in ischemic ARF.

IL-18 and Other Conditions

IL-18 is a mediator of inflammation and tissue injury in many organs. Protection against experimental colitis in caspase-1-deficient mice has been demonstrated as associated with reduced release of IL-18 from the colon. Neutralization of IL-18 during lethal endotoxemia reduces neutrophil tissue accumulation and protects mice against the lethal effects of LPS. Neutrophil activation by IL-18 in vivo has been described. The use of IL-18-neutralizing antiserum has demonstrated the important role of IL-18 in mediating inflammation in models of arthritis, lung injury, and inflammatory bowel disease. In one embodiment, a sample such as blood or joint fluid may be obtained and analyzed for the presence of IL-18 and the presence or concentration of IL-18 may be used to predict inflammatory organ injury such as colotis in the colon.

It would be further helpful for treating physicians to be able to quickly and accurately monitor a patient's predisposition to organ failure, i.e. such as the kidneys after renal injury and before detection of an increase in serum creatinine. It would also be helpful to be able to distinguish changes to the properties of the sample thus a health care provider might be able to monitor the level of key factors in a sample and introduce a therapeutic treatment. In order to monitor the changes caused by a treatment, an assay which evaluates changes to a sample after treatment would also prove useful. However, the present standard for renal failure assessment, the serum creatinine assay, only permits the evaluation of those changes after key events have occurred and this process often leads to death of the patient.

Healthcare professionals have been hindered by an inability to prescribe individualized doses of agents tailored to the unique physiological responses of a particular subject early enough in the process of organ failure. Currently, no known tests are commercially available to determine the early onset of organ failure. In the absence of such data, most treatments are introduced to a patient too late. Early diagnosis and intervention with a treatment such as introduction of fluids, sodium bicarbonate, atrial natriuretic peptides, growth factors, dialysis, or any therapy for prevention of organ failure may either attenuate the progression of the condition or alleviate the symptoms of the condition. Thus, a rapid test to assess the onset of organ failure would be extremely useful for diagnosis and therapeutic monitoring.

Methods

Immunodetection Methods

Antibodies may be generated by any technique known in the art. Antibodies against IL-18 are commercially available, as described below.

In still further embodiments, the present invention concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides. The steps of various useful immunodetection methods have been described in the scientific literature, such as, e.g., Nakamura et al. (1987).

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing IL-18 protein, peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample, such as a tissue section or specimen, a homogenized tissue extract, an isolated cell, a cell membrane preparation, separated or purified forms of any of the above protein-containing compositions or even any biological fluid. Various embodiments include samples where the body fluid is peripheral blood, lymph fluid, ascites, serous fluid, pleural effusion, sputum, cerebrospinal fluid, lacrimal fluid, stool or urine.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined. Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention may be of utility in the diagnosis of various disease states. A biological or clinical sample suspected of containing either the encoded protein or peptide or corresponding antibody is used. However, these embodiments also have applications to non-clinical samples, such as in the titering of antigen or antibody samples, in the selection of hybridomas, and the like.

In the clinical diagnosis or monitoring of patients, the detection of an antigen encoded by a disease state marker nucleic acid, or an increase in the levels of such an antigen, in comparison to the levels in a corresponding biological sample from a normal subject is indicative of a patient with the disease or condition.

Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive. Significant expression may be represented by high levels of antigens in tissues or within body fluids, or alternatively, by a high proportion of cells from within a tissue that each give a positive signal.

Immunohistochemistry

The antibodies of the present invention may be used in conjunction with both fresh-frozen and formalin-fixed, paraffin-embedded tissue blocks prepared by immunohistochemistry (IHC). Any IHC method well known in the art may be used such as those described in *Diagnostic Immunopathology,* 2nd edition. edited by, Robert B. Colvin, Atul K. Bhan and Robert T. McCluskey. Raven Press, New York., 1995, (incorporated herein by reference) and in particular, Chapter 31 of that reference entitled Gynecological and Genitourinary Tumors (pages 579–597), by Debra A. Bell, Robert H. Young and Robert E. Scully and references therein.

ELISA

As noted, it is contemplated that the encoded proteins or peptides of the invention will find utility as immunogens, e.g., in connection with vaccine development, in immunohistochemistry and in ELISA assays. One evident utility of the encoded antigens and corresponding antibodies is in immunoassays for the detection of disease marker proteins, as needed in diagnosis and prognostic monitoring.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and Western blotting, dot blotting, FACS analyses, and the like may also be used.

In one exemplary ELISA, antibodies binding to the encoded proteins of the invention are immobilized onto a selected surface exhibiting protein affinity, such as a well in a polystyrene microtiter plate. Then, a test composition suspected of containing the diseased cells, such as a clinical sample, is added to the wells. After binding and washing to remove non-specifically bound immunecomplexes, the bound antigen may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the disease marker antigen are immobilized onto the well surface and then contacted with the antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the marker protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

Use of Antibodies for Radioimaging

The invention also relates to an in vivo method of imaging a disease condition using the IL-18 antibodies. The antibody, for example, will be labeled by any one of a variety of methods and used to visualize the localized concentration of IL-18 encoded protein. Specifically, this method involves administering to a subject an imaging-effective amount of a detectably-labeled condition-specific monoclonal antibody or fragment thereof and a pharmaceutically effective carrier and detecting the binding of the labeled antibody to the diseased tissue. The term "in vivo imaging" refers to any method which permits the detection of a labeled antibody of the present invention or fragment thereof that specifically binds to a diseased tissue located in the subject's body. A "subject" is a mammal, preferably a human. An "imaging effective amount" means that the amount of the detectably-labeled antibody, or fragment thereof, administered is sufficient to enable detection of binding of the monoclonal antibody or fragment thereof to the diseased tissue.

A factor to consider in selecting a radionuclide for in vivo diagnosis is that the half-life of a nuclide be long enough so that it is still detectable at the time of maximum uptake by the target, but short enough so that deleterious radiation upon the host, as well as background, is minimized. Ideally, a radionuclide used for in vivo imaging will lack a particulate emission, but produce a large number of photons in a 140–2000 keV range, which may be readily detected by conventional gamma cameras.

A radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA). Examples of metallic ions suitable for use in this invention are $^{99m}$Tc, $^{123}$I, $^{131}$I $^{111}$In, $^{131}$I, $^{97}$Ru, $^{67}$Cu, $^{67}$Ga, $^{125}$I, $^{68}$Ga, $^{72}$As, $^{89}$Zr, and $^{201}$Tl.

In accordance with this invention, the antibody or fragment thereof may be labeled by any of several techniques known to the art. The methods of the present invention may also use paramagnetic isotopes for purposes of in vivo detection. Elements particularly useful in Magnetic Resonance Imaging ("MRI") include $^{157}$Gd, $^{55}$Mn, $^{162}$Dy, $^{52}$Cr, and $^{56}$Fe.

Administration of the labeled antibody may be local or systemic and accomplished intravenously, intraarterially, via the spinal fluid or the like. Administration may also be intradermal or intracavitary, depending upon the body site under examination. After a sufficient time has lapsed for the monoclonal antibody or fragment thereof to bind with the diseased tissue, for example 30 minutes to 48 hours, the area of the subject under investigation is examined by routine imaging techniques such as MRI, SPECT, planar scintillation imaging and emerging imaging techniques, as well. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its increase or decrease with time is then monitored and recorded. By comparing the results with data obtained from studies of clinically normal individuals, the presence and concentration of IL-18 may be determined.

Kits

In still further embodiments, the present invention concerns immunodetection kits for use with the immunodetection methods described above. As the encoded proteins or peptides may be employed to detect antibodies and the corresponding antibodies may be employed to detect encoded proteins or peptides, either or both of such components may be provided in the kit. The immunodetection kits will thus comprise, in suitable container means, an encoded protein or peptide, or a first antibody that binds to an encoded protein or peptide, and an immunodetection reagent.

In certain embodiments, the encoded protein or peptide, or the first antibody that binds to the encoded protein or peptide, may be bound to a solid support, such as a column matrix or well of a microtiter plate.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of the encoded protein or polypeptide antigen, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

IL-18 Assay

A non-limiting example of an IL-18 assay may utilize buffered reactant solution as detailed above containing IL-18 antibody. IL-18 antibody (preferably human IL-18 antibody) may be used for the assay. An exemplary buffer solution may comprise Tris-buffered saline solution.

The buffered reactant solution may be added to a sample, such as fresh or freeze-thawed, sample in an assay plate. Samples may further comprise one or more blood, tear or saliva samples. The assay plate may be analyzed in an automated, detector and the presence, absence or concentration of IL-18 can be determined. In a preferred embodiment, the presence of the mature form of IL-18 in a sample may be determined using an ELISA kit (Medical and Biological Laboratories, Nayoga, Japan). A curve may be generated over the course of the assay reactions that has an initial baseline of no IL-18, followed by a progressive rise in the concentration of IL-18.

An IL-18 curve may be generated whereby several parameters of the sample are obtained, relative to that of a simultaneously run standard curve using recombinant human IL-18. Specific measurements may include the IL-18 level itself or the Il-18 level corrected for the amount of serum creatinine.

Particular details of exemplary embodiments of IL-18 assays are provided in the Examples below. However, the skilled artisan will realize that concentrations of various reagents and times and temperatures of reactions may be varied from those specified below without undue experimentation by the person of ordinary skill in the art. Further, where various factors, such as IL-18 antibody are disclosed below, such factors may be substituted with alternative factors known in the art to exhibit similar activities, within the scope of the claimed methods and compositions.

The IL-18 assay is reproducible and analytically sensitive to the IL-18 component in the renal system, as well as to physiologic alterations in progression to organ failure. The measurement of these parameters may be applied to assess subjects with known and as yet undefined organ conditions.

In one embodiment, IL-18 assay results may be analyzed in an individual suffering from renal conditions. Non-limiting examples of renal conditions include but are not limited to ARF, prerenal azotemia, obstructive uropathy, glomerular diseases and interstitial nephritis.

In another embodiment, IL-18 assay results may be analyzed in an individual suffering from a lung condition. Non-limiting examples of lung conditions include but are not limited ARDS (acute respiratory distress syndrome), and ALI (acute lung injury).

In an additional embodiment, IL-18 assay results may be analyzed in an individual undergoing an organ transplant. Non-limiting examples of organ transplants include but are not limited to kidney transplant rejection, delayed function of the kidney transplant and kidney injury.

In yet another embodiment, the IL-18 assay results may be analyzed in healthy subjects to assess organ health in the steady state and in times of altered (pathologic or physiologic) conditions, including the special physiologic states of organ transplant.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Participants and Specimens

The Acute Respiratory Distress Syndrome (ARDS) network is a National Institute of Health (NIH) funded clinical trial consortium conducting studies in ARDS and ALI. A study was performed on a subset of patients enrolled in the trial of low versus high tidal volume ventilation in ARDS and ALI (26, 27). The tidal volume ventilation study was conducted between March 1996 and March 1999 in the 10 ARDS network study centers. The patients were eligible for the ALI studies if they were in the ICU, required positive pressure ventilation and were enrolled within 36 hours of developing ALI. The inclusion and exclusion criteria for these studies was reported previously and is incorporated herein by reference (26, 27). As part of the protocol, urine samples were collected on study days 0, 1 and 3. The urine samples were centrifuged and frozen at −70° C.

In one example of 861 patients of an ARDS Network trial, 617 patients had at least two urine specimens collected as part of the study protocol and 285 patients were excluded with baseline creatinine measurements higher than 1.2 mg/dL. Although ARDS network has chosen the definition of serum creatinine <2 mg/dl for renal failure, in this example 1.2 mg/dl was chosen as the cut-off for the present study to exclude any patients with overt renal dysfunction on day 0. ARF from the remaining 332 patients were selected. Cases were defined as those having irreversible and progressive increase in serum creatinine by at least a 50% increase occurring within the first 6 days of the ARDS study enrollment. There were no urine samples collected after day 3 of the study, thus it would be highly unlikely to detect the presence of any biomarker in the patients who would develop ARF beyond study day 6. The cases of ARF were classified in 6 groups (1 to 6) based on the study day when the creatinine first increased by at least 50%. A total of 52 cases were available with 11, 15, 3, 7, 7, 9 cases who developed ARF from days 1 to 6 respectively. Two controls were randomly selected for every case of ARF on each day from patients who had survived until that day. Due to the considerable number of deaths in the ALI patients, the selection of controls by this method prevented "survivor bias" by reducing the oversampling of survivors. As some patients were randomly chosen more than once as controls, there were 86 controls available for the 52 cases in our study. Altogether, 400 samples of urines were available from cases and controls.

Procedures

Urine IL-18 and urine creatinine was measured in all of the samples. Sodium was measured in the urine from day 0 for estimation of fractional excretion of sodium (FeNa). Urine sodium assays on days 1 and 3 was not performed because corresponding serum sodium values were not available from the ARDS network for estimation of FeNa. Personnel who were blinded to cases and controls performed these biochemical assays. Moreover, specimens were randomly ordered for analysis. The measurements were repeated on 10% of the randomly chosen samples to confirm the reliability of IL-18 results.

In one exemplary method, IL-18 was measured in human urine using a human IL-18 enzyme-linked immunosorbent assay (ELISA) kit (Medical and Biological Laboratories, Nagoya, Japan) that specifically detects the mature form of IL-18 (28). The specificity of this kit for mature IL-18 was confirmed as follows: recombinant human pro-IL-18 (R & D Systems, Minneapolis, Minn.) was assayed using the human IL-18 ELISA kit. One nanogram per milliliter of pro-IL-18 was detected as 10 pg/mL of mature IL-18. Thus, cross-reactivity of the kit for pro-IL-18 is extremely low (21, 25). According to the manufacturer's specifications, the coefficient of variation of interassay and intraassay reproducibility for IL-18 concentration is 5% to 10%. In the present study, reproducibility was identical to that reported by the manufacturer.

Other methods may be used to measure IL-18 in a sample such as Western Blot, RIA (radioimmuno assay), affinity column, chemiluminescent assays as well as devices used for direct measure of IL-18 such as an indicator stick coated with anti-IL-18 antibody. Any method known in the art or in development for IL-18 detection is contemplated herein In one exemplary method, urine creatinine was measured by using Jaffe's colorimetric methodology (Alkaline Picrate). In another exemplary method, urine sodium measurement was performed using Indirect Ion Selective Electrode methodology. In another exemplary method these tests were performed on a Beckman-Coulter LXi725. The intraassay and the interassay coefficients for urine creatinine and urine sodium were 0.8%, 2.5% and 0.5% and 1% respectively.

Variables Available on Patients

In one exemplary method, certain parameters of a subject were assessed as well as evaluating IL-18 in the subject sample(s). Data on baseline demographics (age, gender, race), baseline clinical characteristics (APACHE II (acute physiology assessment and chronic health evaluation), systolic BP, use of vasopressors, cause of lung injury, mechanical ventilation parameters, number of organ failures) and clinical outcomes (survival, ventilator free days) were examples of information available from the ARDS studies (26, 27). In this example, daily serum creatinine was available, but there was no data collected on requirement of renal replacement therapy by the parent studies. Urine output was available on days 0–4, 7 and 14 and serum sodium was available only on day 0. The classification of cases and controls was confirmed by 2 blinded observers who followed the trend in serum creatinine. There was no misclassification error between cases and controls. It was also confirmed that the cases had progressive irreversible increases in creatinine, thereby decreasing the likelihood of pre-renal azotemia as a cause of ARF.

Statistical Analysis

In one example, a primary aim in one analysis was to determine if urine IL-18 was an early marker of ARF. Datasets with demographic, clinical and biochemical variables available 24, 48 and 72 hours before the clinical diagnosis of ARF were obtained. In addition, the role of urine IL-18 in predicting mortality in the ICU was also of interest. Additionally, the distributions of IL-18, serum creatinine and urine output were highly skewed, and the values for these variables were log-transformed before inference testing. A substantial part of all IL-18 measurements were zero values, so it was necessary to increase them by 1 pg/ml before log-transformation.

For univariate analysis of one exemplary method, a comparison among ARF patients and control patients was performed using the Student t test or Mann-Whitney U test for continuous variables and ordinal variables, and categorical data were analyzed with Pearson chi-square test. Logistic regression was employed for multivariable analysis of predictors for early diagnosis of ARF. Odds ratios (OR) and 95% Confidence Intervals (CI) were derived from the model parameter coefficients and standard errors, respectively. In multivariable analyses, confounding by age, sex, tidal volume, oxygenation, sepsis and the APACHE III score were adjusted for each sample. The analysis also included creatinine and urine output which are pivotal for diagnosis of ARF. The Cox Proportional hazards model was employed for examining role of urine IL-18 in predicting time to death. Data were censored at 28 days since the interest was in early mortality. Results are expressed as a mean±SD or median and interdecile range (i.e. between 10–90 percentiles) where appropriate. All tests of significance were two-sided and differences were considered statistically significant with P-value <0.05. The software used for data analysis was R version 1.91 (www.r-project.org) and SAS version 8.2. (SAS Institute, Cary, N.C.)

Study Conduct

The study used data and specimens that were collected as a part of the ARDS network trials and could not be linked to the identifiable patients. The Office of Human Subjects Research granted it an exemption from requirement of review and approval by the Institutional Review Board. The study was also approved by the ARDS network.

Example 1

Patient Characteristics

In one exemplary study, 138 patients were included who were selected from the NIH ARDS network study population. There were 52 study patients who developed ARF in the first 6 days of mechanical ventilation. The remaining 86 patients did not develop ARF and acted as controls for the present study. Day 0 signifies enrollment into the study and occurred within 36 hours of development of ALI. The demographic and clinical characteristics for the 138 patients on Day 0 are shown on Table 1. The mean age of the current study cohort was 50 years with 73% white patients and 52% males. The ARF cases had higher number of patients with sepsis while the controls had higher number of patients with trauma as the precipitating cause of ALI. None of the patients had renal failure on Day 0 (due to the selection criteria), all the patients had respiratory failure, and 42% of cases and 33% of controls had at least one other organ system involved along with respiratory failure. The APACHE III score and the parameters of oxygenation and tidal volume between the two groups were not different. The systolic BP was not different between the 2 groups. However, there was a higher percentage of cases requiring vasopressor drug support in the ARF group (53% vs. 30.2%, P<0.001). Although the serum creatinine was similar between the 2 groups, the urine output was marginally lower in the cases who subsequently developed ARF. None of the patients had oliguria (urine output <400 cc/day) on day 0.

Example 2

Biochemical Measurements on Urine Samples and Patient Outcomes

In one exemplary method, the urine IL-18 values (pg/ml urine) were significantly higher in ARF cases as compared to controls in samples from study days 0, 1, and 3. Similarly, urine IL-18 values corrected for urine dilution (pg/mg creatinine) were significantly higher in ARF cases than in controls. FeNa was comparable in cases and controls on day 0. FeNa could not be calculated for samples on days 1 and 3 because corresponding serum sodium values were not collected by the ARDS network.

Median (interdecile range) urine IL-18 levels in controls with or without sepsis on day 0 were not significantly different [11 (0–454) vs. 0 (0–208), P=0.55]. Similarly the median urine IL-18 levels in ARF cases with or without sepsis on day 0 were not significantly different [257 (0–602) vs. 76 (0–856), p=0.55].

Survival at 28 days and 180 days was also significantly lower in ARF cases as compared to controls. Thus, the short term and long term patient outcomes were poorer in patients who developed ARF as compared to controls. However, the length of stay in the ICU was similar in exemplary cases and controls.

Example 3

Urine IL-18 as an Early Marker for Development of ARF

In another exemplary method, multivariable analyses for predicting ARF were performed separately with data that was available 24 and 48 hours (Table 3A and 3B, respectively) before the clinical diagnosis of ARF. In one prediction of ARF, urine IL-18 values on days 0, 1 and 3 were taken for patients who developed ARF on days 1, 2 and 4, respectively. After multivariable analysis and combining ARF cases with corresponding controls on those days, urine IL-18 values 24 hours before the development of ARF were highly significant in predicting the development of ARF after adjusting for other baseline and clinical characteristics (Table 3A). The urine IL-18 values were highly significant in predicting the development of ARF after adjusting for demographic variables, sepsis, tidal volume, APACHE III, corresponding serum creatinine and urine output levels 24 hours before diagnosis. The presence of sepsis itself did not predict development of ARF in the study patients. The APACHE III score on day 0 was also independently predictive of development of ARF after 24 hours. The adjusted OR suggested that for an increase in urine IL-18 value by 25 pg/ml the odds of development of ARF in next 24 hours increased by 19% (P=0.0056).

In this exemplary method, the multivariable analysis for prediction of ARF 48 hours before diagnosis, included urine IL-18 values on days 0, 1 and 3 on patients who developed ARF on days 2, 3 and 5, respectively. Urine IL-18 was significantly associated with the development of ARF after 48 hours and adjusting for other clinical parameters as discussed in the above analysis (Table 3B). However, the adjusted OR for urine IL-18 values was 9% for an increase in urine IL-18 by 25 pg/ml compared to 18% for the predictive analysis from 24 hours before diagnosis. In one example, multivariable analysis for predicting ARF 72 hours before the clinical diagnosis of ARF did not reveal urine IL-18 a significance at this time (data not shown). Other more sensitive detection methods for measuring IL-18 in a sample may be used to analyze samples taken more than 48 hours before clinical diagnosis of ARF.

Example 4

Performance Characteristics of Urine IL-18 as a Diagnostic Marker 24 Hours Before Clinical Diagnosis In one exemplary method demonstrated in FIG. 1 the sensitivity, specificity, positive predictive value (PPV) and negative predictive value (NPV) for various cut-offs of urine IL-18 for predicting ARF within the next 24 hours are disclosed. A urine IL-18 value of 20 pg/ml has a sensitivity of 75% and a NPV of 84% for development of ARF within next 24 hours. In contrast, a urine IL-18 value of 200 pg/ml has a specificity of 91% and PPV of 68%. The area under the ROC curve (receiver operating curve) for the urine IL-18 test is 73%, demonstrating a good performance for the diagnosis of ARF within the next 24 hours. The performance of the ROC curve for the early diagnosis of ARF before 48 hours was 65%.

In this exemplary method an ROC curve is generated. An ROC curve is a plot of test sensitivity (plotted on the y axis) versus its False Positive Rate (or 1—specificity) (plotted on the x axis). Each point on the graph is generated by using a different cut point. The set of data points generated from the different cut points is the empirical ROC curve. Lines are used to connect the points from all the possible cut points. The resulting curve illustrates how sensitivity and the FPR vary together.

Example 4

Figure 2:
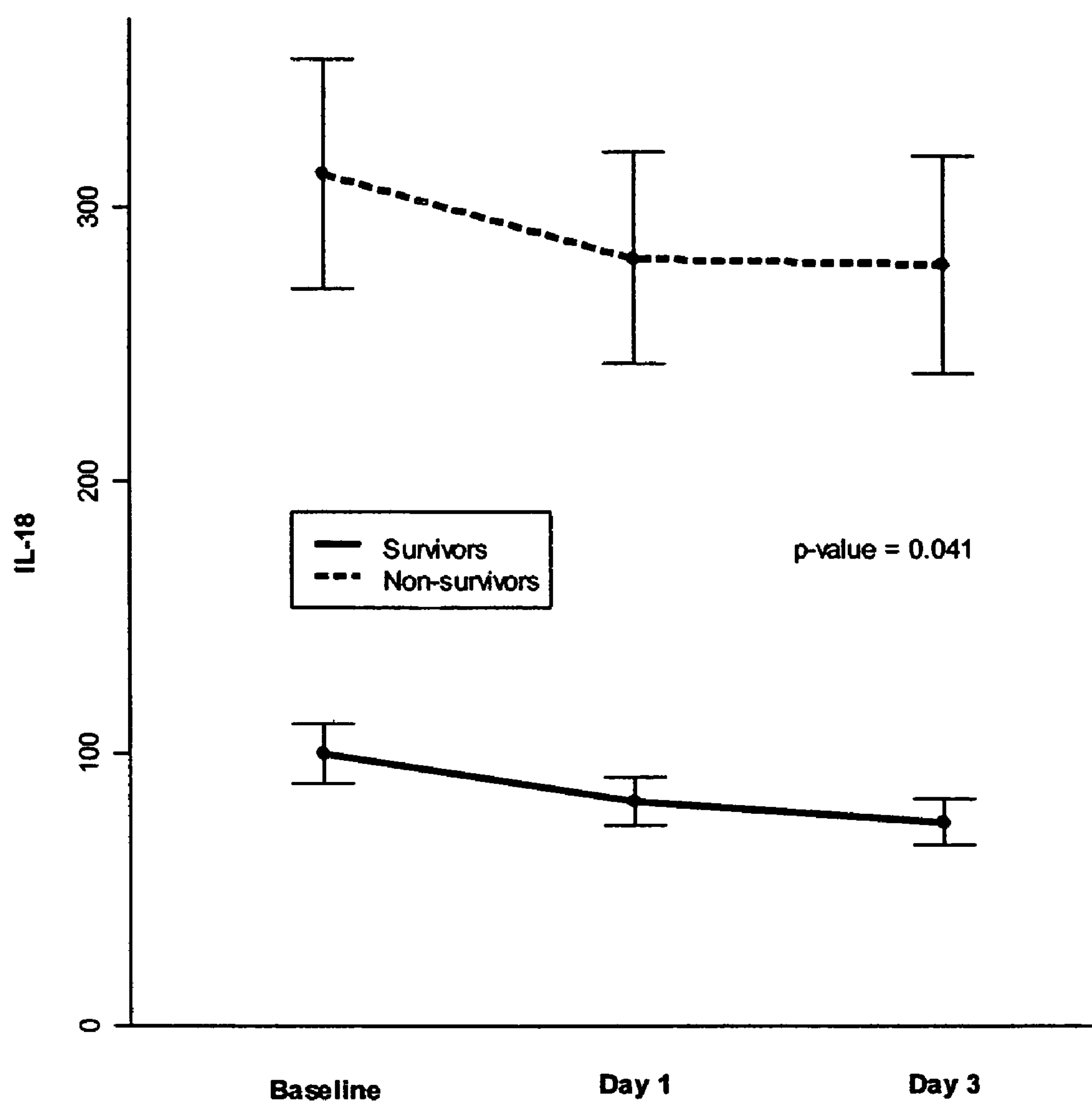
FIG. 2 represents an exemplary curve of survivors (-) and non-survivors (---) and IL-18 concentration on Day 0, 1 and 3.

Urine IL-18 Levels and Mortality (FIG. 2 and Table 4)

In one exemplary technique, FIG. 2 represents a clear and significant separation of survivors and non-survivors at 28 days based on the urine IL-18 values on days 0, 1 and 3 (P=0.04). The Cox proportional hazards analysis for predicting time to death demonstrates that the urine IL-18 value on day 0 is the strongest predictor of death in the ICU after adjusting for APACHE III score and other baseline and clinical parameters. An increase in urine IL-18 value by 1 ng/ml increases the odds of death by 2.5 fold.

Other Cytokines

Several studies have shown that circulating levels of pro or anti-inflammatory cytokines correlate with prognosis of sepsis and the development of multiorgan failure (34–38). For example increases in serum concentrations of IL-6, IL-8, IL-10, TNF-α and IL-18 all are associated with poor outcome in sepsis and predict multi-organ dysfunction (34–40). There are, however, important distinctions between the detection of IL-18 and other cytokines in critically ill patients. One distinction is that in most studies, these cytokines have been studied in serum or plasma. The measurement of these cytokines in urine has not yet been performed to assess and validate their prognostic role in a critical care setting. Herein, the presence of cytokines in the urine can offer a simpler and easier alternative than using serum measurements. Secondly, many of these studies are performed in the presence of sepsis, thereby limiting the role of the test in other critical care settings. As noted in the Example section there was no significant effects of sepsis on urine IL-18 levels in ARF cases or controls. Third, studies herein measure cytokines at different time points during the course of illness. Thus, the results of association with mortality are conflicting between these studies. The present study correlated the independent association of urine IL-18 with mortality measured at the time of mechanical ventilation, which is a well defined point in the clinical course of a critically ill patient.

All of the COMPOSITIONS and/or METHODS and/or APPARATUS disclosed and claimed herein can be made and executed without undue experimentation in light of the present disclosure. While the compositions and methods of this invention have been described in terms of preferred embodiments, it will be apparent to those of skill in the art that variation may be applied to the COMPOSITIONS and/or METHODS and/or APPARATUS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES 1. de Mendonca A, Vincent J L, Suter P M, et al. Acute renal failure in the ICU: risk factors and outcome evaluated by the SOFA score. Intensive Care Med 2000;26(7):915–21.
2. Groeneveld A B, Tran D D, van der Meulen J, Nauta J J, Thijs L G. Acute renal failure in the medical intensive care unit: predisposing, complicating factors and outcome. Nephron 1991;59(4):602–10.
3. Hoste E A, Lameire N H, Vanholder R C, Benoit D D, Decruyenaere J M, Colardyn F A. Acute renal failure in patients with sepsis in a surgical ICU: predictive factors, incidence, comorbidity, and outcome. J Am Soc Nephrol 2003;14(4):1022–30.
4. Metnitz P G, Krenn C G, Steltzer H, et al. Effect of acute renal failure requiring renal replacement therapy on outcome in critically ill patients. Crit Care Med 2002;30(9):2051–8.
5. Lien J, Chan V. Risk factors influencing survival in acute renal failure treated by hemodialysis. Arch Intern Med 1985;145(11):2067–9.
6. Abreo K, Moorthy A V, Osborne M. Changing patterns and outcome of acute renal failure requiring hemodialysis. Arch Intern Med 1986;146(7):1338–41.
7. Biesenbach G, Zazgornik J, Kaiser W, Grafinger P, Stuby U, Necek S. Improvement in prognosis of patients with acute renal failure over a period of 15 years: an analysis of 710 cases in a dialysis center. Am J Nephrol 1992;12(5):319–25.
8. Parikh C R, McSweeney P A, Korular D, et al. Renal dysfunction in allogeneic hematopoietic cell transplantation. Kidney Int 2002;62(2):566–73.
9. Shusterman N, Strom B L, Murray T G, Morrison G, West S L, Maislin G. Risk factors and outcome of hospital-acquired acute renal failure. Clinical epidemiologic study. Am J Med 1987;83(1):65–71.
10. Chertow G M, Levy E M, Hammermeister K E, Grover F, Daley J. Independent association between acute renal failure and mortality following cardiac surgery. Am J Med 1998;104(4):343–8.
11. Levy E M, Viscoli C M, Horwitz R I. The effect of acute renal failure on mortality. A cohort analysis. Jama 1996;275(19):1489–94.
12. Star R A. Treatment of acute renal failure. Kidney Int 1998;54(6):1817–31.
13. Rabb H. Novel urinary markers for early diagnosis of ARF. Am J Kidney Dis 2003;42(3):599–600.
14. Muramatsu Y, Tsujie M, Kohda Y, et al. Early detection of cysteine rich protein 61 (CYR61, CCN1) in urine following renal ischemic reperfusion injury. Kidney Int 2002;62(5):1601–10.
15. Han W K, Bailly V, Abichandani R, Thadhani R, Bonventre J V. Kidney Injury Molecule-1 (KIM-1): a novel biomarker for human renal proximal tubule injury. Kidney Int 2002;62(1):237–44.
16. Mishra J, Ma Q, Prada A, et al. Identification of neutrophil gelatinase-associated lipocalin as a novel early urinary biomarker for ischemic renal injury. J Am Soc Nephrol 2003;14(10):2534–43.

17. Hirschberg R, Kopple J, Lipsett P, et al. Multicenter clinical trial of recombinant human insulin-like growth factor I in patients with acute renal failure. Kidney Int 1999;55(6):2423–32.

18. Allgren R L, Marbury T C, Rahman S N, et al. Anaritide in acute tubular necrosis. Auriculin Anaritide Acute Renal Failure Study Group. N Engl J Med 1997;336(12):828–34.

19. Stone G W, McCullough P A, Tumlin J A, et al. Fenoldopam mesylate for the prevention of contrast-induced nephropathy: a randomized controlled trial. Jama 2003;290(17):2284–91.

20. Star R. Design issues for clinical trials in acute renal failure. Blood Purif 2001;19(2):233–7.

21. Melnikov V Y, Ecder T, Fantuzzi G, et al. Impaired IL-18 processing protects caspase-1-deficient mice from ischemic acute renal failure. J Clin Invest 2001;107(9): 1145–52.

22. Melnikov V Y, Faubel S, Siegmund B, Lucia M S, Ljubanovic D, Edelstein C L. Neutrophil-independent mechanisms of caspase-1- and IL-18-mediated ischemic acute tubular necrosis in mice. J Clin Invest 2002;110(8): 1083–91.

23. Dinarello C A. Biologic basis for interleukin-1 in disease. Blood 1996;87(6):2095–147.

24. Fantuzzi G, Puren A J, Harding M W, Livingston D J, Dinarello C A. Interleukin-18 regulation of interferon gamma production and cell proliferation as shown in interleukin-1beta-converting enzyme (caspase-1)-deficient mice. Blood 1998;91(6):2118–25.

25. Parikh C R, Jani A, Melnikov V Y, Faubel S, Edelstein C L. Urinary interleukin-18 is a marker of human acute tubular necrosis. Am J Kidney Dis 2004;43(3):405–14.

26. Ventilation with lower tidal volumes as compared with traditional tidal volumes for acute lung injury and the acute respiratory distress syndrome. The Acute Respiratory Distress Syndrome Network. N Engl J Med 2000; 342(18):1301–8.

27. Ketoconazole for early treatment of acute lung injury and acute respiratory distress syndrome: a randomized controlled trial. The ARDS Network. JAMA 2000;283 (15):1995–2002.

28. Shibata M, Hirota M, Nozawa F, Okabe A, Kurimoto M, Ogawa M. Increased concentrations of plasma IL-18 in patients with hepatic dysfunction after hepatectomy. Cytokine 2000;12(10):1526–30.

29. Kwon O, Molitoris B A, Pescovitz M, Kelly K J. Urinary actin, interleukin-6, and interleukin-8 may predict sustained ARF after ischemic injury in renal allografts. Am J Kidney Dis 2003;41(5):1074–87.

30. du Cheyron D, Daubin C, Poggioli J, et al. Urinary measurement of Na+/H+ exchanger isoform 3 (NHE3) protein as new marker of tubule injury in critically ill patients with ARF. Am J Kidney Dis 2003;42(3):497–506.

31. Westhuyzen J, Endre Z H, Reece G, Reith D M, Saltissi D, Morgan T J. Measurement of tubular enzymuria facilitates early detection of acute renal impairment in the intensive care unit. Nephrol Dial Transplant 2003;18(3): 543–51.

32. Miller T R, Anderson R J, Linas S L, et al. Urinary diagnostic indices in acute renal failure: a prospective study. Ann Intern Med 1978;89(1):47–50.

33. Zarich S, Fang L S, Diamond J R. Fractional excretion of sodium. Exceptions to its diagnostic value. Arch Intern Med 1985;145(1):108–12.

34. Pinsky M R, Vincent J L, Deviere J, Alegre M, Kahn R J, Dupont E. Serum cytokine levels in human septic shock. Relation to multiple-system organ failure and mortality. Chest 1993;103(2):565–75.

35. Gogos C A, Drosou E, Bassaris H P, Skoutelis A. Pro- versus anti-inflammatory cytokine profile in patients with severe sepsis: a marker for prognosis and future therapeutic options. J Infect Dis 2000;181(1):176–80.

36. Casey L C, Balk R A, Bone R C. Plasma cytokine and endotoxin levels correlate with survival in patients with the sepsis syndrome. Ann Intern Med 1993;119(8):771–8.

37. Ahlstrom A, Hynninen M, Tallgren M, et al. Predictive value of interleukins 6, 8 and 10, and low HLA-DR expression in acute renal failure. Clin Nephrol 2004;61 (2):103–10.

38. Simmons E M, Himmelfarb J, Sezer M T, et al. Plasma cytokine levels predict mortality in patients with acute renal failure. Kidney Int 2004;65(4):1357–65.

39. Ranieri V M, Giunta F, Suter P M, Slutsky A S. Mechanical ventilation as a mediator of multisystem organ failure in acute respiratory distress syndrome. Jama 2000;284(1):43–4.

40. Emmanuilidis K, Weighardt H, Matevossian E, et al. Differential regulation of systemic IL-18 and IL-12 release during postoperative sepsis: high serum IL-18 as an early predictive indicator of lethal outcome. Shock 2002; 18(4):301–5.

TABLE 1

| Variable | ARF (N = 52) | No ARF (N = 86) | P-Value |
|---|---|---|---|
| Age (Mean ± SD) | 50 ± 18.6 | 50.4 ± 16 | 0.9 |
| Gender | | | |
| Male | 42.3% | 58.1% | 0.07 |
| Ethnicity | | | 0.07 |
| White non-Hispanic | 73.1% | 73.3% | |
| Black non-Hispanic | 21.2% | 17.4% | |
| Hispanic | 0.0% | 7.0% | |
| Other | 5.8% | 2.3% | |
| Precipitating Factor | | | 0.005 |
| Trauma | 5.8% | 24.4% | |
| Sepsis | 30.8% | 15.1% | |
| Pneumonia | 44.2% | 36% | |
| Aspiration | 5.8% | 15.1% | |
| Other | 13.5% | 9.3% | |
| Non-pulmonary or renal organ failure | | | 0.4 |
| 1 other organ | 42.3% | 33.7% | |
| 2 other organs | 32.7% | 30.2% | |
| 3 other organs | 7.7% | 8.1% | |
| 4 other organs | 3.8% | 3.5% | |
| Apache III (Mean ± SD) | 77 ± 20 | 73 ± 25 | 0.3 |
| PaO2/FiO2 < 200 | 84.6% | 74.4% | 0.15 |
| Vasopressors | 53.8% | 30.2% | 0.006 |
| Systolic BP (Mean ± SD) mm of Hg | 97 ± 27 | 102 ± 23 | 0.25 |
| Ventilation Protocol | | | 0.5 |
| 6 ml/kg | 52% | 57% | |
| 12 ml/kg | 48% | 43% | |
| Renal Characteristics (Day 0) | | | |
| Median Serum Creatinine (mg/dl) | 0.85 | 0.90 | 0.3 |
| Range | (0.5–1.1) | (0.5–1.1) | |
| Median Urine Output (liters) | 1.9 | 2.5 | |
| Range | (0.7–4.5) | (1.4–5.8) | 0.004 |

TABLE 2

| Test | ARF | No ARF | P-value |
|---|---|---|---|
| Urine IL-18 (pg/ml)[1] | | | |
| Day 0 | 126 (0–795) | 0 (0–275) | 0.001 |
| Day 1 | 65 (0–576) | 0 (0–214) | 0.001 |
| Day 3 | 88 (0–574) | 0 (0–205) | 0.0004 |
| Urine IL-18/creatinine[1] (pg/mg) | | | |
| Day 0 | 156 (0–1785) | 0 (0–581) | 0.0003 |
| Day 1 | 134 (0–1316) | 0 (0–401) | 0.0008 |
| Day 3 | 171 (0–1970) | 0 (0–472) | 0.0004 |
| FeNa (%) | | | |
| Day 0 | 1.06 ± 1.6 | 1.12 ± 1.6 | NS |
| Patient Outcomes | | | |
| Mortality % | | | |
| 28-day Mortality | 57.7% | 19.8% | <0.0001 |
| 180-day Mortality | 63.5% | 25.6% | <0.0001 |
| Length of stay in ICU (Mean ± SD) | 19.3 ± 28.4 | 19.8 ± 22.3 | NS |

[1]Values are medians and 10–90th percentile

TABLE 3A

| Variables | Adjusted OR | 95% CI | P-Value |
|---|---|---|---|
| Age (every 10 years) | 0.96 | 0.9–1.2 | 0.8 |
| Female Gender | 1.5 | 0.5–4.9 | 0.4 |
| Tidal volume: 12 ml/kg group | 1.35 | 0.4–4.1 | 0.6 |
| APACHE III score (every 10 unit) | 1.34 | 1–1.5 | 0.02 |
| Sepsis | 1.95 | 0.5–7.1 | 0.3 |
| PaO2/FiO2 (every 1 unit) | 0.997 | 0.99–1.007 | 0.9 |
| Creatinine 1 day before ARF | 3.7 | 0.5–24 | 0.16 |
| Output 1 day before ARF (every 1 liter) | 0.7 | 0.45–1.14 | 0.16 |
| IL-18 pg/ml 1 day before ARF (every 25 units) | 1.18 | 1.05–1.29 | 0.0056 |

TABLE 3B

| Variables | Adjusted OR | 95% CI | P-Value |
|---|---|---|---|
| Age (every 10 years) | 1 | 0.9–1.5 | 0.5 |
| Female Gender | 2.8 | 0.7–10.5 | 0.1 |
| Tidal volume: 12 ml/kg group | 0.9 | 0.2–3.1 | 0.8 |
| APACHE III score (every 10 units) | 0.99 | 0.96–1.02 | 0.84 |
| Sepsis | 2.3 | 0.6–8.33 | 0.19 |
| PaO2/FiO2 (every 1 unit) | 1 | 0.99–1.01 | 0.45 |
| Creatinine 2 day before ARF | 4 | 0.5–31.5 | 0.18 |
| Urine Output 2 day before ARF (every 1 liter) | 0.96 | 0.65–1.4 | 0.87 |
| IL-18 pg/ml 2 day before ARF (every 25 units) | 1.09 | 1.025–1.16 | 0.02 |

TABLE 4

| Variables | Hazards Ratio | 95% CI | P-Value |
|---|---|---|---|
| Age (every 10 years) | 1.2 | 1.08–1.4 | 0.004 |
| Female Gender | 0.41 | 0.2–0.82 | 0.01 |
| Tidal volume: 12 ml/kg group | 2.45 | 1.3–4.5 | 0.003 |
| APACHE III (every 10 units) | 1.22 | 1.07–1.3 | 0.001 |
| Sepsis | 1.25 | 0.61–2.56 | 0.53 |
| PaO2/FiO2 (every 1 unit) | 0.995 | 0.991–1.0 | 0.04 |
| Baseline Creatinine | 0.54 | 0.15–1.91 | 0.34 |
| Baseline Urine Output (every 1 liter) | 0.91 | 0.78–1.05 | 0.2 |
| Baseline IL-18 ng/ml (every 1 unit) | 2.56 | 1.74–3.78 | <0.00001 |

What is claimed is:

1. A method for diagnosing acute renal failure in a subject comprising:

identifying a subject having acute respiratory distress syndrome (ARDS) or acute lung injury (ALI) not currently diagnosed with acute renal failure (ARF);

measuring the concentration of serum creatinine in the subject;

obtaining a urine sample from the subject prior to elevated serum creatinine in the subject, wherein elevated serum creatinine is indicated by a 50% increase of serum creatinine concentration above a baseline concentration of serum creatinine in the subject wherein the baseline serum creatinine is equal to or less than 1.2 mg/dl;

assessing the concentration of interleukin 18 (IL-18) protein in the sample; and diagnosing the presence of ARF in the subject prior to elevated serum creatinine concentration based on an increased concentration of IL-18 protein in the sample relative to a normal control subject.

2. The method of claim 1, wherein IL-18 protein is detected using an anti-IL-18 antibody.

3. The method of claim 2, wherein using an anti-IL-18 antibody for detecting IL-18 protein further comprises using an ELISA assay for analyzing the concentration of IL-18 protein in the sample.

4. The method of claim 2, wherein the anti-IL-18 antibody comprises an antibody that detects the pro or mature form of IL-18 protein.

5. The method of claim 1, further comprising collecting and testing more than one sample for the concentration of IL-18 protein from the subject.

6. The method of claim 5, wherein the samples are collected at different time intervals.

7. The method of claim 6, wherein samples are collected over a period of minutes, hours, and/or days following an event.

8. The method of claim 7, wherein an event comprises the admittance of a subject to the intensive care unit of a medical facility.

9. The method of claim 7, wherein an event comprises an injury to a kidney.

10. The method of claim 1, wherein diagnosing ARF in the subject comprises diagnosing ARF in the subject when the concentration of IL-18 protein in the sample is greater than or equal to 100 pg/ml.

11. A method for diagnosing acute renal failure in a subject comprising:

identifying a subject having acute respiratory distress syndrome (ARDS) or acute lung injury (ALI) not currently diagnosed with acute renal failure (ARF);

measuring the concentration of serum creatinine in the subject;

obtaining a urine sample from the subject prior to elevated serum creatinine in the subject, wherein elevated serum creatinine is indicated by a 50% increase of serum creatinine concentration above a baseline concentration of serum creatinine in the subject wherein the baseline serum creatinine is equal to or less than 1.2 mg/dl;

assessing the concentration of interleukin 18 (IL-18) protein in the sample; and diagnosing the presence of ARF in the subject up to 48 hours prior to elevated serum creatinine concentration based on the concentration of IL-18 protein in the sample wherein the concentration of IL-18 protein in the sample is greater than or equal to 100 pg/ml.

* * * * *